US009063111B2

(12) United States Patent
Acevedo et al.

(10) Patent No.: US 9,063,111 B2
(45) Date of Patent: Jun. 23, 2015

(54) HYBRID CHEMICAL SENSOR, AND, SENSITIVE POLYMERIC COMPOSITION

(75) Inventors: Edwin Moncada Acevedo, Barrio Boston (CO); Gilvan Pozzobon Pires, Menino Deus (BR); João Henrique Zimnoch Dos Santos, Independencia (BR)

(73) Assignees: Braskem S.A., Camacari (BR); Universidade Federal do Rio Grande do Sul, Porto Alegre-RS (BR)

( * ) Notice: Subject to any disclaimer, the term of this patent is extended or adjusted under 35 U.S.C. 154(b) by 836 days.

(21) Appl. No.: 13/001,851

(22) PCT Filed: Jun. 22, 2009

(86) PCT No.: PCT/IB2009/052681
§ 371 (c)(1),
(2), (4) Date: Apr. 21, 2011

(87) PCT Pub. No.: WO2010/001298
PCT Pub. Date: Jan. 7, 2010

(65) Prior Publication Data
US 2012/0009687 A1    Jan. 12, 2012

(30) Foreign Application Priority Data

Jun. 30, 2008  (BR) ..................................... 0805080
Jun. 16, 2009  (BR) ..................................... 0901318

(51) Int. Cl.
*G01N 31/22* (2006.01)
(52) U.S. Cl.
CPC ............ *G01N 31/221* (2013.01); *Y10T 436/17* (2015.01); *Y10T 436/175383* (2015.01); *Y10T 436/173845* (2015.01)

(58) Field of Classification Search
USPC ................. 422/400, 402, 408, 416, 420, 430, 422/82.05–82.09; 436/20–21, 111–113, 436/129, 133, 135–136, 163–164, 166, 169, 436/172
See application file for complete search history.

(56) References Cited

U.S. PATENT DOCUMENTS

| | | | | |
|---|---|---|---|---|
| 3,963,442 | A * | 6/1976 | Bullard et al. | ................ 436/165 |
| 3,998,591 | A * | 12/1976 | Eckfeldt | ................... 422/82.11 |
| 4,001,587 | A * | 1/1977 | Panchenkov et al. | ...... 250/474.1 |
| 4,050,895 | A * | 9/1977 | Hardy et al. | .................. 436/527 |
| 4,251,282 | A * | 2/1981 | Vahlensieck et al. | ......... 106/481 |
| 4,399,099 | A * | 8/1983 | Buckles | ........................ 422/401 |
| 4,948,843 | A * | 8/1990 | Roberts et al. | ............. 525/328.2 |
| 5,043,285 | A * | 8/1991 | Surgi | ............................ 436/136 |
| 5,047,350 | A * | 9/1991 | Switalski et al. | ............. 436/136 |
| 5,100,970 | A * | 3/1992 | Roberts et al. | ................ 525/342 |
| 5,114,676 | A * | 5/1992 | Leiner et al. | ............... 422/82.06 |
| 5,200,334 | A | 4/1993 | Dunn et al. | |
| 5,219,527 | A * | 6/1993 | Hui et al. | ................... 422/82.06 |

(Continued)

OTHER PUBLICATIONS

Zaggout, F. R. Materials Letters 2006, 60, 1026-1030.*

(Continued)

*Primary Examiner* — Arlen Soderquist
(74) *Attorney, Agent, or Firm* — Duane Morris LLP

(57) ABSTRACT

The present invention relates to chemical sensors with hybrid characteristics, which are thermo-mechanically stable and able to respond to changes in the environment, particularly in the presence of amine and/or amide and/or oxide-reducing compounds, and/or vapor thereof by color change, as well as its incorporation into sensitive polymeric composition.

5 Claims, 2 Drawing Sheets

<--- Strong Pink

<---- Yellow

(56) References Cited

U.S. PATENT DOCUMENTS

Figure 1A:
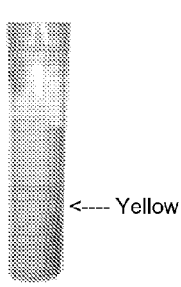
Figure 1B:
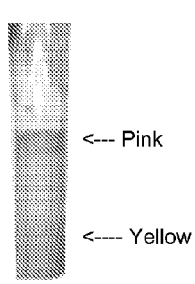
Figure 1C:
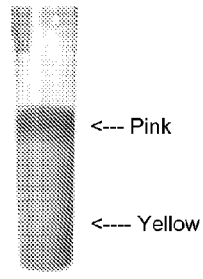
Figure 1D:
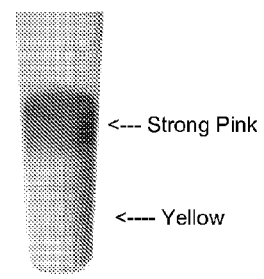

| | | | |
|---|---|---|---|
| 5,280,548 A * | 1/1994 | Atwater et al. | 385/12 |
| 5,292,801 A * | 3/1994 | Avnir et al. | 525/54.1 |
| 5,300,564 A * | 4/1994 | Avnir et al. | 525/54.1 |
| 5,399,609 A * | 3/1995 | Moss | 524/423 |
| 5,408,999 A * | 4/1995 | Singh et al. | 600/342 |
| 5,439,979 A * | 8/1995 | Mack et al. | 525/218 |
| 5,480,582 A * | 1/1996 | Pope | 252/301.4 F |
| 5,489,988 A * | 2/1996 | Ackley et al. | 356/436 |
| 5,496,997 A * | 3/1996 | Pope | 250/227.21 |
| 5,501,836 A * | 3/1996 | Myerson | 422/400 |
| 5,637,507 A * | 6/1997 | Wicks et al. | 436/166 |
| 5,650,331 A * | 7/1997 | Jorgensen et al. | 436/163 |
| 6,015,715 A * | 1/2000 | Kirschner et al. | 436/166 |
| 6,022,748 A * | 2/2000 | Charych et al. | 436/527 |
| 6,235,532 B1 * | 5/2001 | Uttamchandani et al. | 436/60 |
| 6,241,948 B1 * | 6/2001 | Watkins et al. | 422/82.05 |
| 6,262,187 B1 * | 7/2001 | Minami et al. | 525/464 |
| 6,313,219 B1 * | 11/2001 | Taylor-Smith | 524/853 |
| 6,330,464 B1 * | 12/2001 | Colvin et al. | 600/316 |
| 6,340,443 B1 * | 1/2002 | Kurihara et al. | 264/464 |
| 6,383,815 B1 * | 5/2002 | Potyrailo | 436/2 |
| 6,485,987 B1 * | 11/2002 | Charych et al. | 436/535 |
| 6,495,368 B1 * | 12/2002 | Wallach | 436/20 |
| 6,562,424 B1 * | 5/2003 | Reisfeld et al. | 428/34.7 |
| 6,602,716 B1 * | 8/2003 | Klimant | 436/172 |
| 6,699,717 B1 * | 3/2004 | Rao et al. | 436/39 |
| 6,730,212 B1 * | 5/2004 | Yamagishi et al. | 205/777.5 |
| 6,794,191 B2 * | 9/2004 | Putnam et al. | 436/1 |
| 6,952,436 B2 * | 10/2005 | Wirnsberger et al. | 372/39 |
| 7,014,816 B2 * | 3/2006 | Miller et al. | 422/87 |
| 7,393,693 B2 * | 7/2008 | Anvar et al. | 436/176 |
| 7,652,767 B2 * | 1/2010 | Harsh et al. | 356/445 |
| 7,740,904 B2 * | 6/2010 | Shahriari | 427/157 |
| 7,858,380 B2 * | 12/2010 | Baker et al. | 436/127 |
| 7,862,770 B2 * | 1/2011 | Shahriari | 422/420 |
| 8,026,328 B2 * | 9/2011 | Rowell | 528/10 |
| 8,173,440 B2 * | 5/2012 | Paolacci et al. | 436/167 |
| 8,287,637 B2 * | 10/2012 | Carlini et al. | 106/481 |
| 8,790,930 B2 * | 7/2014 | Mills et al. | 436/113 |
| 2002/0044891 A1 | 4/2002 | Miller et al. | 422/56 |
| 2002/0065366 A1 | 5/2002 | Wirnsberger et al. | 525/88 |
| 2002/0128542 A1 | 9/2002 | Van Over | 600/310 |
| 2003/0008400 A1 * | 1/2003 | Putnam et al. | 436/1 |
| 2003/0018109 A1 * | 1/2003 | Hsiao et al. | 524/269 |
| 2003/0062263 A1 * | 4/2003 | Stanford et al. | 204/403.01 |
| 2003/0068827 A1 * | 4/2003 | Morris et al. | 436/136 |
| 2003/0082321 A1 * | 5/2003 | Kennedy et al. | 428/35.7 |
| 2003/0143118 A1 * | 7/2003 | Draaijer | 422/82.06 |
| 2003/0211011 A1 * | 11/2003 | Phillips et al. | 422/82.05 |
| 2004/0081384 A1 * | 4/2004 | Datesman et al. | 385/12 |
| 2004/0131806 A1 * | 7/2004 | Barmore et al. | 428/34.2 |
| 2006/0154414 A1 * | 7/2006 | Lin | 438/222 |
| 2006/0257094 A1 * | 11/2006 | McEvoy et al. | 385/147 |
| 2007/0079748 A1 * | 4/2007 | Ahmed et al. | 116/206 |
| 2007/0122311 A1 * | 5/2007 | Shahriari | 422/82.11 |
| 2007/0196656 A1 * | 8/2007 | Rowell | 428/403 |
| 2008/0026217 A1 * | 1/2008 | Kim et al. | 428/357 |
| 2008/0199360 A1 * | 8/2008 | Shahriari | 422/82.06 |
| 2008/0220534 A1 * | 9/2008 | Paolacci et al. | 436/128 |
| 2008/0297799 A1 * | 12/2008 | Caron et al. | 356/432 |
| 2009/0061226 A1 * | 3/2009 | Banin et al. | 428/402 |
| 2009/0246674 A1 * | 10/2009 | Carlini et al. | 430/110.2 |
| 2009/0285258 A1 * | 11/2009 | Kinami | 374/102 |
| 2010/0036491 A1 * | 2/2010 | He et al. | 623/11.11 |
| 2010/0140502 A1 * | 6/2010 | Guckian et al. | 250/459.1 |
| 2010/0171043 A1 * | 7/2010 | Burke et al. | 250/459.1 |
| 2010/0197027 A1 * | 8/2010 | Zhang et al. | 436/66 |
| 2010/0279428 A1 * | 11/2010 | Rhee et al. | 436/172 |
| 2012/0276647 A1 * | 11/2012 | Mills et al. | 436/113 |

OTHER PUBLICATIONS

Zink, J. I. et al, "Inorganic Sol-Gel Glasses as Matrices for Nonlinear Optical Materials" ACS Symposium Series, vol. 455, Materials for Nonlinear Optics, Chapter 36, 1991, 541-552.*
Yang, L. et al, Analytical Chemistry 1995, 67, 1307-1314.*
Saegusa, T., Pure & Applied Chemistry 1995, 67, 1965-1970.*
Bekiari, V. et al, Journal of Non-Crystalline Solids 1998, 226, 200-203.*
Wolfbeis, O. S. et al, Analytica Chimica Acta 1986, 185, 321-327.*
Wolfbeis, O. S. et al, Mikrochimica Acta 1986 III 359-366.*
Parker, J. W. et al, Analytical Chemistry 1993, 65, 2329-2334.*
Werner, T. et al, Analyst 1995, 120, 1627-1631.*
Brandenburg, A. et al, Mikrochimica Acta 1995, 121, 95-105.*
Lobnik, A. et al, Analyitca Chimica Acta 1998, 367, 159-165.*
Malins, C. et al, Sensor and Actuators B 1998, 51, 359-367.*
Malins, C. et al, Thin Solid Films 2000, 368, 105-110.*
Lobnik, A. et al, Sensor and Actuators B 2001, 74, 194-199.*
Dong, S. et a, Sensor and Actuators B 2008, 129, 94-98.*

* cited by examiner

<--- Yellow

<--- Pink
<--- Yellow

<--- Pink
<--- Yellow

<--- Strong Pink
<--- Yellow

Golden

Yellowish Green

Orange

Yellow --> 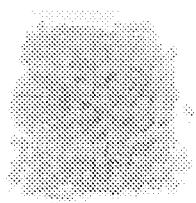  Translucent -->  Brown --> 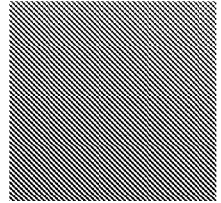
Figure 3a                    Figure 3b                    Figure 3c
Rosy --> 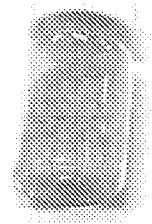  Pink -------> ◯  Strong Pink --> 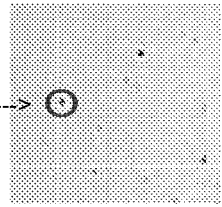
Figure 3d                    Figure 3e                    Figure 3f

HYBRID CHEMICAL SENSOR, AND, SENSITIVE POLYMERIC COMPOSITION

TECHNICAL FIELD

The present invention relates to chemical sensors which may be incorporated into polymeric matrices, without any loss in their chemical characteristics during polymer processing.

The chemical sensors of the present invention have organic-inorganic hybrid characteristics, and they are thermo-mechanically stable and able to respond to changes in the environment, particularly in the presence of amine and/or amide and/or oxide-reducing compounds, and/or vapor thereof by color change.

BACKGROUND OF THE INVENTION

Chemical sensors can be defined as devices able to detect the presence and/or concentration of a certain group of chemicals or a specific substance. Sensors in which the detection of a certain substance occurs by color change have the advantage of an immediate visual analysis via visual observation, calorimetric methods or image analysis.

The technological improvement related to detecting and signaling the presence of at least one chemical compound has been developed to seek new chemical sensors that exhibit the characteristics of lower costs, short response time to a specific color change, reliability (eliminating the possibility of a false response) and higher sensitivity.

In this context, many chemical sensors have been prepared using the sol-gel technology. The sol-gel material provides high surface area, narrow pore size distribution and purity. The sol-gel acts as a sorbent material capable of sampling, retaining, concentrating and releasing compounds.

The international publication WO1993/04196 reports about a porous glassy structure containing a biologically active encapsulated material able to detect through photometric techniques the quantitative and qualitative presence of several organic or inorganic compounds, especially enzymes. However, that application does not describe that said porous glassy structure obtained presents good thermal stability and good mechanical stability.

The patent application US 2007/0161069 reports about the invention of biosensor compounds from complex Ruthenium compounds and an enzyme. The claimed product acts through the fluorescence of ruthenium compounds, which occurs in the ultraviolet (UV) region. Although the substrate used may be polymeric, the application does not mention that the biosensor obtained presents good thermal or mechanical stability; additionally, its response takes place in the UV region, which restrains its use as a sensor that is visible to the naked eye.

The international publication WO/2006/086197 A2 describes obtaining sensor elements used for measuring the concentration of gaseous substances from "cytochrome c" embedded in a sol-gel matrix. Once again, in that document, thermal and mechanical stability data for the sensor obtained are not described.

The patent application US 2007/0071789 introduces bioactive materials used for medical implants, which are formed by drugs encapsulated in a sol-gel reaction. The drugs are released to the organism for long periods at body temperature, data about this bio-active material at high temperatures or under mechanical strain conditions are not described.

Another patent application, US 2006/0154414, presents a sensor compound applied to the detection and removal of contaminants, such as pesticides and insecticides. In spite of the sensor's good thermal stability indicated in that application, their use is difficult when they are mixed in polyolefinic compounds due to the incompatibility between the sensor and the polyolefinic matrix.

The patent application US 2006/0172431 reports about a sol-gel encapsulated hexanuclear Molybdenum/Tungsten cluster, with 12 anionic ligands for in vivo and in vitro biological monitoring of the oxygen content. Substituted metallic structures, such as that of Tungsten used in this compound, show low thermal stability.

Finally, the patent application US 2006/0267094 presents a sensor for carbon dioxide (($CO_2$) and for a $CO_2/O_2$ combination and the use of this sensor in films composed by Terephthalate Polyethylene (PET), Polyethylene (PE) and PET/PE blends, by printing laminated films. Due to the low thermal stability, the sensor is applied to the film surface and, thus, acts as a sensor, which makes the packaging manufacturing process more complex, slower and more expensive.

Standing out among the most widely used sensors are those for detecting oxygen from both living and non-living organisms, in addition to sensors sensitive to organic compounds such as sugars and amino acids, among others. Usually, these types of sensors have neither thermal nor mechanical stability to be industrially processed.

On the other hand, the extreme conditions on which polymers are processed are well known, especially in what concerns temperature and shear forces. Therefore, if chemical sensors will be used as filler in polymer matrices, as suggested by the present invention, there are essential properties, such as high thermal stability at high temperatures, high stability to shear forces and good compatibility with the polymeric phase, which must be observed.

The sensors described in the prior art references mentioned above fail to present thermal and mechanical stability, particularly at high temperatures and shear forces, do not have characteristics which may favor their compatibility with polymers.

Accordingly, there was a need for sensors with good compatibility with polyolefin matrices, which improves its dispersion in the polymeric mass during processing and, consequently, provides better effectiveness for its sensory properties.

The sensor of the present invention presents good compatibility with the polyolefin matrix used and also thermal and mechanical stability. Therefore, they can be mixed with polymers by conventional extrusion procedures, which usually takes place at temperatures about 150° C.-300° C., without losing their activity. Such effect is indicated by a color change in the presence of amines and amides, as well as in the presence of any substance that may change the sensor's pH, such as, for example, oxide-reducing compounds and vapors thereof. In interacting with the sensor or with the sensor incorporated in a polymeric matrix, these substances make the sensor show a color change.

The state-of-the-art literature does not describe or suggest the subject matter described and claimed in the present application, since it does not present a thermally and mechanically stable chemical sensor with hybrid characteristics able to respond to pH changes in the presence of amine, amide and oxide-reducing compounds by changing color through direct contact and/or through the vapors thereof.

The sensitive polymeric composition containing the sensor of the present invention incorporated there into may be used in the food, pharmaceutical, environmental, petrochemical and analytical detection industries.

SUMMARY OF THE INVENTION

The present invention relates to chemical sensors which may be incorporated into polymeric matrices, without any loss in their chemical characteristics during polymer processing.

The chemical sensors of the present invention have organic-inorganic hybrid characteristics, and thermo-mechanical stability, and they are able to respond to changes in the environment, particularly in the presence of amine and/or amide and/or oxide-reducing compounds, and/or vapor thereof by color change.

The present invention also consists of incorporation of these sensors into polymeric matrices, wherein the material resulting there from (hereinafter called "sensitive polymeric composition") may be used in the food, pharmaceutical, petrochemical and environmental industries, among others.

The method for incorporating these sensors into polymer resins is carried out by extrusion using conventional processing conditions, that is, high temperatures (until 300° C.) and high shear forces.

The present invention is also related to the products obtained from the incorporation of the sensors into polymeric matrices.

The sensor, according to the present invention, particularly comprises the following components:

a) A compound sensitive to changes in the characteristics of the environment in which it is being used, by color change;

b) A capsule having the sensitive compound obtained through sol-gel reaction techniques using alkoxides, particularly siliceous and/or titanium alkoxides, to provide thermal and mechanical stability and hybrid characteristics.

The sensor so obtained is then incorporated into the polymeric matrix by known processing techniques, so that the final material can be used for a variety of applications.

Thus, the present invention describes sensors of different compounds that change their color as a response to the analytic. The sensor has sensitive compounds that change their color according to the chemical elements released in the environment to which it has been exposed The sensitive compounds may be selected, for example, from anthocyanins, bromocresol purple, bromocresol green, methyl red, phenol red, cresol red, bromothymol blue and 4-nitrophenol; or also from sensitive compounds that change their color under oxidation and reduction conditions, such as N-phenanthranilic acid, resazurin and ferroin.

The sensitive compounds are encapsulated by hybrid material generated by a sol-gel reaction. The goal of the encapsulation is to provide the sensors with hybrid and thermal and mechanical stability characteristics that allow them to be used in polymeric matrices, which are processed at high temperatures and the end product may be used in the food, pharmaceutical, petrochemical and environmental industries. Those sensors which fail to provide the above mentioned characteristics cannot be used in polymer processing.

DETAILED DESCRIPTION

The sensors of the present invention are obtained through the following steps:

a) Preparing a sensitive compound solution;

b) Adding the sol-gel reaction components by hydrolytic reaction or non-hydrolytic reaction, setting the reaction time and temperature conditions, siliceous/water ratio or titanium/water ratio, type of catalyst, and pH value;

c) Obtaining the sensors in a suspension or powder form.

It is important to stress that at least one of the alkoxides used in item b must be substituted with one or more alkyl groups. The substituting alkyl groups are responsible for the good compatibility of the sensor with the polymeric matrix.

In the context of the present application, it is understood as "alkoxide substituted by an alkyl group", an alkoxide having at least an alkyl group directly bonded to the metallic atom thereof. In other words, there must be at least one bond C-M wherein M is a metal atom.

Finally, once a properly encapsulated sensor having hybrid characteristics has been obtained, the final step consists of incorporating it into a polymeric matrix through the conventional processing usually used for polymer additivation.

In the course of the present report, the expressions below have the following meaning:

Sol-gel reactions: hydrolytic reaction via base or acid catalysis or non-hydrolytic reaction catalyzed by a Lewis acid ($FeCl_3$, $AlCl_3$, etc). Both employ different siliceous or titanium alkoxides as precursors and regulators of the final properties of the material.

Hydrolytic reaction: reaction employing alkoxides, water, acid or base, carried out at controlled temperature, time and stirring.

Non-hydrolytic reaction: reaction employing siliceous or titanium alkoxides, siliceous tetrachloride ($SiCl_4$), Lewis acid, carried out at controlled temperature, time and stirring.

Thermal stability: consists of the ability of the sensor to endure resin processing temperatures without changing its characteristics.

Mechanical stability: consists of the ability of the sensor to endure the shear stress generated in resin processing without changing its characteristics.

Hybrid: compound with organic and inorganic characteristics.

The preparation of the sensitive compound solution is carried out by dissolving a certain amount of this compound into a certain amount of solvent. The amounts of the sensitive compound range from 0.01 grams to 5 grams dissolved in 1.0 mL to 100 L of solvent, at room temperature, and wide concentration ranges are achieved.

Once the solution has been obtained, the sol-gel reaction compounds are added. Initially, the pH value is set by adding an acid or base known to state of the art. After the desired pH has been achieved, siliceous or titanium alkoxides are added in order to encapsulate the sensitive compound, thus providing a sensor having hybrid characteristics. When one wants to achieve a powder sensor, the reaction medium has to be solidified and subsequently milled, washed and dried.

Encapsulation by adding siliceous or titanium alkoxides takes place by controlling the type of alkoxides, pH, temperature, time, and alkoxide/water ratio. By setting these variables, one can control particle size, morphology, and the relative percentage of organic and inorganic groups, that is, the compound's degree of hybridity.

The determination of the type of siliceous or titanium alkoxides, alkoxide/water ratio and pH variables allows its morphology to be determined.

Temperature, pH and time variation is responsible for determining particle size.

The siliceous alkoxides used are preferably ethyltriethoxysilane, methyltriethoxysilane, phenyltriethoxysilane, methyltrimethoxysilane, n-octylethoxysilane and n-butylethoxysilane. The titanium alkoxides used are preferably tetraethoxytitanium, ethylethoxytitanium, methyltriethoxytitanium, phenyltriethoxytitanium, n-octylethoxytitanium, n-butylethoxytitanium.

The presence of siliceous and titanium provides the sensor with thermal and mechanical stability characteristics, hybridity being ensured by the type and number of substitutions in the structure of the alkoxide used. Accordingly, the hybrid chemical sensor of the present invention comprises sensitive compounds encapsulated by a hybrid capsule obtained by sol-gel reaction, wherein the hybrid capsule uses siliceous and/or titanium alkoxides, in which at least one of the alkoxides is substituted with one or more alkyl groups. In embodiments, the hybrid chemical sensor presents a spherical, fibrillary, laminar or amorphous morphology.

The hybrid sensor described and claimed by the present invention is used as an indicator of conditions in a particular environment, food, surface, compound, etc., in contact with said sensor.

As indicated, the present invention is applied to packaging in general, environments of which the conditions must be known, such as workplaces, and analytic for identifying and quantifying chemical compounds in analytical chemistry.

Some better understanding can be achieved by looking at the following examples, which are described herein for illustrative purpose only, not limiting the means by which the invention can be carded out.

EXAMPLES

For better understanding of the present invention, examples relative to the tests for the present invention are presented below.

The following examples are related to obtaining sensors, their activity of identifying analytic and the incorporation of these sensors into polymeric matrices.

The sensitive compounds shown in Table 1 are examples of compounds that can be used for preparing the chemical sensor of the present invention.

TABLE 1

| Sensitive Compounds | Structure | Range of pH change | Decomposition (° C.) |
|---|---|---|---|
| Anthocyanins | 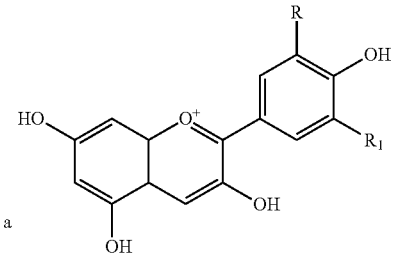 | 1-14[b] | — |
| Bromocresol purple | 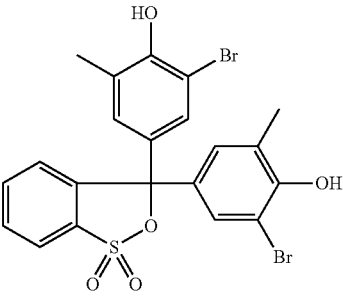 [SMILES: Cc1cc(C2(c3cc(C)c(O)c(Br)c3)OS(=O)(=O)c3ccccc32)cc(Br)c1O] | 5.2-6.8 | 241 |
| Bromocresol green | 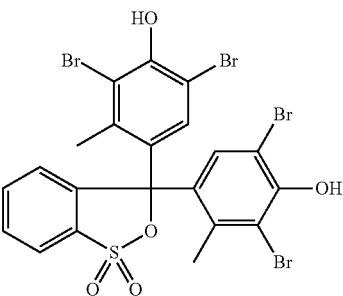 [SMILES: Cc1c(C2(c3cc(Br)c(O)c(Br)c3C)OS(=O)(=O)c3ccccc32)cc(Br)c(O)c1Br] | 3.8-5.4 | 218 |

Characteristics of sensitive compounds used for sensor preparation.

TABLE 1-continued

Characteristics of sensitive compounds used for sensor preparation.

| Sensitive Compounds | Structure | Range of pH change | Decomposition (° C.) |
|---|---|---|---|
| Methyl red | 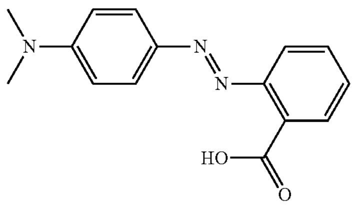 [SMILES: CN(C)c1ccc(/N=N/c2ccccc2C(=O)O)cc1] | 4.4-6.2 | 175 |
| Phenol red | 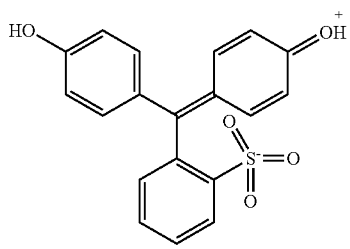 | 6.8-8.4 | 285 |
| Cresol red | 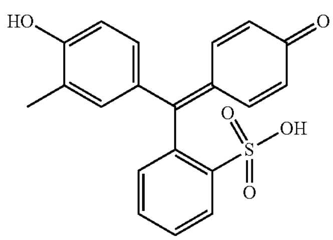 [SMILES: Cc1cc(C(=C2C=CC(=O)C=C2)c2ccccc2S(=O)(=O)O)ccc1O] | 7.2-8.0 | 250 |
| Bromothymol blue | 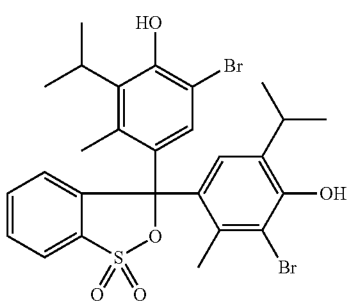 [SMILES: Cc1c(C2(c3cc(Br)c(O)c(C(C)C)c3C)OS(=O)(=O)c3ccccc32)cc(C(C)C)c(O)c1Br] | 6.0-7.6 | 204 |
| 4-nitrophenol | 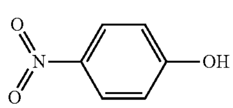 | 5.0-7.0 | 279 |
| N-phenanthranilic acid | 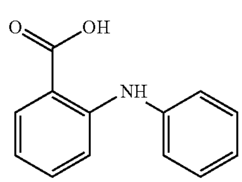 [SMILES: O=C(O)c1ccccc1Nc1ccccc1] | Redox | 187 |
| Resazurin | 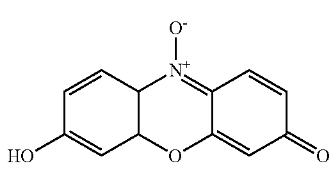 [SMILES: O=C1C=CC2=[N+]([O-])C3C=CC(O)=CC3OC2=C1] | Redox | 273 |

TABLE 1-continued

Characteristics of sensitive compounds used for sensor preparation.

| Sensitive Compounds | Structure | Range of pH change | Decomposition (° C.) |
|---|---|---|---|
| Ferroin | [structure] | Redox | — | a R and $R_1$ substituents can be H, OH and $OCH_3$.
b Different colors are observed all across the pH range.

Example 1

Sensor Preparation and Confirmation of Sensor Effectiveness at Different Temperatures The sensitive compound was encapsulated through a sol-gel reaction, which provides the sensitive compound with mechanical and thermal stability, in addition to hybrid surface characteristics. Furthermore, a sensor effectiveness test was performed at room temperature and at 300° C. The methodology used is described below.

The sensor was obtained by the following methodology: 9.0 mg of the sensitive compound (phenol red) was dispersed in a mixture of 8.1 mL TEOS (tetraethylorthosilicate), 5.0 mL MTMS (methyltrimethoxysilane). Subsequently, 9.7 mL of 0.2 M HCl was added. The compound reacts for 1 hour at room temperature and under mechanical stirring. After this time has elapsed, the solid is milled to a particle size in the order of microns, washed with water until the washing residue becomes colorless and then is dried in an oven at 80° C. Finally, a chemical sensor in the form of a yellow powder is obtained.

In order to confirm the sensing effect, the sensor obtained in example 1 was subjected to a gaseous base ($NH_3$) at room temperature. The solid begins to show a red color when it reacts with ammonia, which confirms its sensitivity to the detection of amine compounds at room temperature.

In order to confirm the sensing effect at high temperatures, a test was performed at 300° C. with the sensor obtained in Example 1. In this assay, mineral oil (EMCA350) heated at 300° C. was used in the presence of the sensor, remaining at this temperature for 2 minutes and being cooled down to room temperature. After reaching room temperature, $NH_3$ was subjected to bubbling and a color change from yellow to red was observed at high temperatures.

FIG. 1 shows the four stages, with different colors, which the material undergoes when the atmosphere changes at room temperature. In the first stage (FIG. 1a), the material shows a yellow color. In the second stage (FIG. 1b), with addition of $NH_3$ gas, the material begins to show a pink color in the upper portion and the color is increasingly enhanced as shown in stages 3 (FIGS. 1c) and 4 (FIG. 1d) until a strong pink hue is reached, indicating a pH change in the middle of the process, and it does not return to its original color anymore.

Figure 2A:
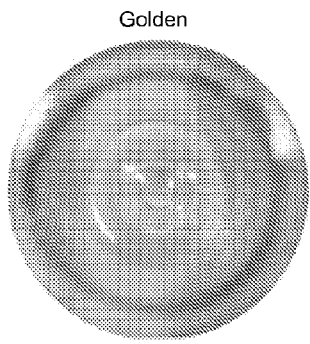
Figure 2B:
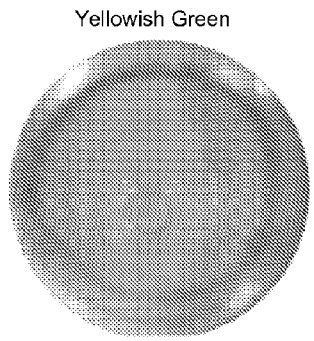
Figure 2C:
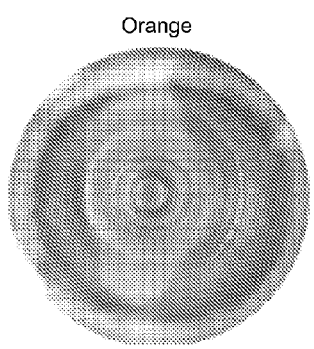

FIG. 2 shows three stages of the oil at a temperature of 300° C.; in the first stage, the oil is seen without the sensor, displaying a golden color (FIG. 2a); the second stage shows the oil with the sensor (FIG. 2b), in a yellowish green color, in a 2-minute time interval; and in the third stage (FIG. 2c), the oil is shown at room temperature with the sensor and the analyte (gaseous base), which causes a color change to an orange hue. The color change is demonstrated to occur only in the medium in which the gaseous base is bubbled, confirming the sensing effect vis-à-vis the analyte and the sensor's thermal stability at 300° C.

FIG. 3 shows a color change in a resin, films and parts made of materials containing sensors. FIG. 3a shows pellets of a material without interaction with ammonia, displaying a yellow color. FIG. 3b shows a translucent film of the material without interaction with ammonia, and FIG. 3c shows a brown-colored part without interaction with ammonia. FIG. 3d shows pink-colored pellets of a material after interacting with ammonia. FIG. 3e shows a film with pink spots after interacting with ammonia, and FIG. 3f shows the part, already displaying a strong pink hue, after the material has interacted with ammonia.

Example 2

Incorporation of the Sensor into a Polymeric Matrix and Confirmation of its Effectiveness at High Temperatures The incorporation of the sensor into a polymeric matrix was carried out using standard extrusion procedures, such as temperature profile, type of screw and type of extruder usually employed in an additivation process. After the sensor was incorporated into the polymer, films were made in a blown film extruder, and parts were injected using an injection machine. The thickness of the films was 10-80 µm. The injected parts had thicknesses between 1-4 mm.

In order to confirm the sensor's thermal stability after being incorporated into a polymeric matrix through color change of the pellet, film and injected part, these were exposed to ammonia vapors. in FIG. 3, a color change can be observed in the materials described, confirming the sensor's stability at temperatures used for resin additivation (sensor incorporation), as well as at temperatures for processing/ injection/extrusion of materials obtained from these resins, such as films and injected parts, which demonstrates the sensor's thermal stability in two consecutive thermal processes.

These films and injected parts, composed of a resin that has been processed twice, the first time for incorporating the sensor and the second one for producing the film or part, show color change in the presence of base compounds such as amines. For the pellets, a color change from yellow to red can be observed after an interaction with base compounds. For the film, which is initially translucent, the presence of red colored spots is observed after an interaction with ammonia, and, finally, a color change from brown to red is observed in the injected part in the presence of ammonia compounds.

With this, both the sensor's color change after being dispersed through the polymeric matrix, when in contact with ammonia vapors, and the thermal and mechanical stability of the sensor under the polyolefin processing conditions are demonstrated.

It must be evident for those skilled in the art that the present invention can be embodied in more than one specific way without deviating from the spirit or scope of the invention. Particularly, it must be understood that the invention can be embodied in the described forms.

Therefore, the present examples and embodiments must be considered illustrative and not limitative, and the invention must not be limited to the details provided in this document, but it can be modified within the scope and equivalence of the annexed claims.

The invention claimed is:

1. A hybrid chemical sensor comprising a sensitive compound completely dispersed within a polyolefin matrix and encapsulated by a hybrid capsule obtained by sol-gel reaction, said hybrid capsule using siliceous alkoxides or titanium alkoxides, wherein at least one of said alkoxides is substituted with one or more alkyl chains, wherein the hybrid chemical sensor responds to the presence of amine and/or amide and/or oxide-reducing compounds, and/or vapor thereof by color change after being dispersed through the polyolefin matrix, and wherein the hybrid chemical sensor is incorporated into the polyolefin matrix by extrusion and without any loss in chemical characteristics during polyolefin processing, and is used as an indicator of conditions in a particular environment in contact with said hybrid chemical sensor.

2. The hybrid chemical sensor according to claim 1, wherein the hybrid capsule is stable up to a temperature of 300° C. and endures the shear stress generated in standard extruders.

3. The hybrid chemical sensor according to claim 1, wherein said siliceous alkoxides are selected from the group consisting of tetraethoxysilane (TEOS), ethyltrimethoxysilane (ETMS), methyltrimethoxysilane (MTMS), phenyltrimethoxysilane (PTMS), n-octylethoxysilane, or n-butylethoxysilane.

4. The hybrid chemical sensor according to claim 1, wherein said titanium alkoxides are selected from the group consisting of tetraethoxytitanium, ethyltriethoxytitanium, methyltriethoxytitanium, phenyltriethoxytitanium, n-octylethoxytitanium, or n-butylethoxytitanium.

5. The hybrid chemical sensor according to claim 1, wherein the hybrid chemical sensor presents a spherical, fibrillary, laminar or amorphous morphology.

* * * * *